(12) United States Patent
Goldiner

(10) Patent No.: US 7,563,096 B2
(45) Date of Patent: Jul. 21, 2009

(54) ANOMALOUS SYNTHETIC TOOTH ARRANGEMENT

(76) Inventor: Arthur H. Goldiner, 431 Leoni Dr., Grover Beach, CA (US) 93433

( * ) Notice: Subject to any disclaimer, the term of this patent is extended or adjusted under 35 U.S.C. 154(b) by 343 days.

(21) Appl. No.: 10/795,691

(22) Filed: Mar. 6, 2004

(65) Prior Publication Data

US 2005/0196728 A1 Sep. 8, 2005

(51) Int. Cl.
*A61C 5/08* (2006.01)
(52) U.S. Cl. ........................ 433/229; 433/218
(58) Field of Classification Search ............... 433/229, 433/218–219, 168.1, 183, 171, 214
See application file for complete search history.

(56) References Cited

U.S. PATENT DOCUMENTS

| | | | |
|---|---|---|---|
| 2,057,341 A | 10/1936 | Morgan | |
| 3,558,540 A * | 1/1971 | Molnar | 523/109 |
| 4,251,215 A | 2/1981 | May et al. | |
| 5,324,198 A | 6/1994 | Hazen | |
| 5,403,186 A | 4/1995 | Ginsburg | |
| 5,451,498 A | 9/1995 | Hazen | 433/167 |
| 5,547,381 A | 8/1996 | Nutting | 433/218 |
| 5,569,036 A | 10/1996 | Goldiner et al. | 433/168.1 |
| 5,709,548 A * | 1/1998 | Oxman et al. | 433/218 |
| 5,775,909 A | 7/1998 | Langer | 433/218 |
| 5,951,291 A | 9/1999 | Albert et al. | 433/215 |

OTHER PUBLICATIONS

Esthetic Success, CDA. Journal. vol. 32. No. 2. Feb. 2004.

"Effect of fillers and vulcanizing systems on the physicomechanical* and electrical properties of EPDM vulcanizates," M. N. Ismail; G. M. Turky Polymer-Plastics Technology and Engineering, vol. 40, Issue 5, Nov. 2001, pp. 635-652. 1 page (* alternate spelling of physio-mechanical properties.).
"Dentin Crown Surface of Human Adult Incisor Teeth," Robert N. Staley, vol. 47, No. 5, J Dent Res Sep.-Oct. 1968; 5 pages.
"Microstructure of Dental Enamel. I. Organization and Contour of Prisms," Robert Hoffman and Leo Gross, Waldemar Medical Research Foundation, Inc., Woodbury, New York, vol. 46, No. 6, J. dent. Res. Nov.-Dec. 1967; 12 pages.
Foothills Ltd., "Custom Dracula Fangs and Custom Werewolf Fangs", 1994.
Generik Ink, Inc., "Why Not Party? Custom Fangs", 1989.
Violets, "Professional Fangtastics", *1996 Halloween Show Flyer*, Violets, a division of RAM Southwest, Inc. 1996.

* cited by examiner

*Primary Examiner*—John J Wilson
(74) *Attorney, Agent, or Firm*—Thomas F. Lebens; Sinsheimer Juhnke Lebens & McIvor, LLP

(57) ABSTRACT

Novelty synthetic dental arrangements having one or more anomalous appearing synthetic novelty teeth. In an embodiment, the anomalous appearing synthetic novelty teeth include an interior cavity for filling with an acrylic based plastic impression material and directly coupling to a natural tooth. In another embodiment, a synthetic denture assembly which incorporates a plurality of individual synthetic novelty teeth bound to a synthetic gum element. Both novelty synthetic dental arrangements are held in position by a generally rigid curing impression material which forms a custom fir with the user's teeth when cured. The impression material utilizes dental grade reagents including an isobutyl methacrylate based monomer, a dibutyl phthalate based plasticizer and an amyl acetate based solvent. Additional chemical components are present in the impression material precursors.

29 Claims, 6 Drawing Sheets

ANOMALOUS SYNTHETIC TOOTH ARRANGEMENT

CROSS-REFERENCE TO RELATED APPLICATIONS

Not applicable.

FEDERALLY SPONSORED RESEARCH AND DEVELOPMENT

Not applicable.

REFERENCE TO A MICROFICHE APPENDIX

Not Applicable.

FIELD OF INVENTION

The present invention relates generally to novelty dental arrangement and more specifically to a method, dental apparatus and kit for producing an anomalous synthetic dental arrangement for temporary placement over or in front of one or more natural human teeth.

BACKGROUND

There are several types of permanent artificial tooth caps. Dental bridges are intended to fill gaps between teeth by securing prefabricated artificial teeth to the remaining natural teeth. Crowns are cemented in place over a carefully prepared tooth that has been specially shaped and ground to receive the crown. Posts that receive permanent crowns may be fastened to studs inserted into upper or lower jaw bones. Crowns are functional realistic tooth caps temporarily or permanently cemented in place to repair a damaged natural tooth. Partials are functional teeth that fill gaps from missing teeth which can be inserted and removed at will by the user. All of these prosthetics are custom made and are generally intended for extended functional use and wear rather than for novelty or strictly non-functional ornamentation or appearance.

Novelty teeth for the purposes of changing the appearance of a user's tooth or teeth temporarily are known in the relevant art. For example, U.S. Pat. No. 5,569,036 to Goldiner, et al., the instant inventor, discloses an anatomically disproportionate prefabricated fang shaped tooth cap. The aforementioned patent, U.S. Pat. No. 5,569,036 to the instant inventor is herein incorporated by reference in its entirety. The tooth cap includes an interior cavity that is filled with a resilient, flexible impression material. The set impression material provides a soft, flexible impression of the user's tooth inside the cap which adheres by suction and surface tension at a saliva/impression material interface.

From the inventor's experience, a disadvantage associated with resilient dental impression materials is the minimal formation of physio-mechanical interlocks with natural contour, interstitial spaces or surface profile variations of the natural tooth such as ridges, undercuts, depressions, pits, cracks, pores, etc.

In another example, U.S. Pat. No. 5,547,381 to Nutting, discloses a synthetic novelty tooth cap that is used in conjunction with a low melt thermoplastic to form a partial plate that is affixed to adjacent teeth. The Nutting reference incorporates ridges and depressions within the synthetic novelty tooth cap to provide greater expansion area for the low melt thermoplastic. One disadvantage associated with the Nutting invention, is that the partial plate arrangement is cosmetically unsightly as the partial plate is generally visible, detracting from the overall novelty appearance of the fang tooth. Secondly, fitting of the synthetic novelty tooth assembly entails a level of skill necessary to provide a reasonably secure fit which usually necessitates a trial and error fitting effort by the user.

In another example, U.S. Pat. No. 5,775,909 to Langer, discloses a synthetic novelty tooth in the form a fang. The synthetic novelty tooth is constructed of digestible constituents to reduce the risk of internal damage due to accidental consumption of the tooth. The synthetic novelty tooth is affixed to a user's tooth by the adherence properties of the digestible constituents alone. A main disadvantage of this synthetic novelty tooth arrangement is the limited useful life of the tooth due to attack on the synthetic novelty tooth by natural digestive juices and enzymes present in saliva.

In a final example, U.S. Pat. No. 5,951,291 to Albert, et al., discloses a novelty denture arrangement that simulates the appearance of an assemblage of teeth. The denture arrangement is held in place by somewhat resilient materials such as cured silicone rubbers which intercalate the gaps of the teeth.

The use of silicone rubbers may be suitable for short term usage but will generally degrade over time due to physical tearing during repeated installations and removals by the user. Likewise, the resilient nature of the silicone rubber limits the attachment strength due to minimal formation of physio-mechanical interlocks with the underlying nature teeth as described above.

Therefore, a need exists in the relevant art to produce a high quality novelty dental arrangement which requires little or no skill to use, provides a tight fit with one or more underlying natural teeth, is comfortable to wear and remains in place with no unsightly attachment materials visible.

SUMMARY

This invention addresses the limitations described above and provides a method, apparatus produced by the method, apparatus and a kit for producing an anomalous appearing synthetic denture device. In one embodiment of the invention, a prefabricated novelty synthetic tooth is provided which includes an interior cavity. In an alternate embodiment of the invention, a plurality of synthetic novelty teeth bound to at least a front side of a somewhat flexible synthetic gum element is provided.

A generally rigid curing impression material is used in both embodiments of the invention to form a rigid impression of one or more of the user's teeth. In the individual tooth embodiment of the invention, the impression material is disposed into the interior cavity of the synthetic novelty tooth. The synthetic novelty tooth is then coaxially positioned over a desired human tooth such that the interior cavity encapsulates at least a portion of the human tooth. The synthetic novelty tooth is left in place a sufficient amount of time for the generally rigid curing impression material to cure.

In the integrated synthetic novelty teeth and gum embodiment of the invention, the generally rigid curing impression material is applied to a rear surface of the synthetic gum element and arranged such that the generally rigid curing impression material encounters one or more of the user's teeth and allowed to remain in place until the impression material has sufficient time to cure.

The generally rigid curing impression material forms a tight physio-mechanical fit with a plurality of natural contour variations, interstitial spaces, undercuts, etc. associated with the human tooth or teeth when cured. These contour variations include elevations, depressions and ridges present in the natural enamel of the selected human tooth. When desired to be used, the synthetic denture device is affixed to the human tooth in which the generally rigid curing impression material originally cured. Reaffixing of the synthetic novelty tooth is accomplished by coaxially positioning the tooth over the human tooth and providing sufficient force to overcome the resistance generated by the tight fit.

In an embodiment of the invention, the sufficient amount of time to allow the generally rigid curing impression material to cure is less than 10 minutes. In another embodiment of the invention, the sufficient amount of time to allow the generally rigid curing impression material to cure is in a range of 3 to 10 minutes. In an embodiment of the invention, the generally rigid curing impression material is essentially transparent when cured.

In various embodiments of the invention, the chemical constituents utilized in the generally rigid curing impression material include at least one alkyl-acrylic monomer selected from the group consisting of isobutyl methacrylate, methyl methylacrylate, ethyl methacrylate, N-butyl methacrylate, trimethylolpropane trimethacrylate and polymethyl methacrylate.

The generally rigid curing impression material further includes at least one alkyl-phthalate ester plasticizer selected from the group consisting of dialkyl phthalate, dibutyl phthalate and N,N-dimethyl-p-toluidine.

The generally rigid curing impression material further includes at least one organic solvent selected from the group consisting of denatured ethanol, amyl acetate, ethyl acetate and isobutyl acetate. The generally rigid curing impression material generally includes a volumetric mixture ratio relative to an isobutyl methacrylate based monomer of approximately 2 parts of said isobutyl methacrylate based monomer, 1 part of a dibutyl phthalate based plasticizer and 0.5 part of an amyl acetate based solvent.

In embodiments of the invention, the isobutyl methacrylate based monomer consists essentially of a volumetric mixture of 80-90% isobutyl methacrylate and 10-20% trimethylolpropane trimethacrylate.

In an embodiment of the invention, the dibutyl phthalate based plasticizer consists essentially of a volumetric mixture of 75-85% dibutyl phthalate and 15-25% denatured ethanol.

In embodiments of the invention, the amyl acetate based solvent consists essentially of a volumetric mixture of 94-100% amyl acetate, 0-5% ethyl acetate and 0-1% isobutyl acetate.

In various embodiments of the invention, the synthetic novelty teeth may be made from a variety of compositions selected from the group consisting of an alkyl acrylic based plastic, an acrylonitrile butadiene styrene based plastic, a polyethylene based plastic, a polycarbonate based plastic, a nylon based plastic, porcelain, stainless steel, titanium, silver and gold.

In various embodiments of the invention the anomalous appearing synthetic denture device includes at least one tooth form selected from the group consisting of one or more non-homosapien teeth, metal encapsulated teeth, decayed teeth, deformed teeth, misaligned teeth, spicate (spike-shaped) teeth, sudiform (stake-like) teeth, stipiform (stalk-like) teeth, cuneate (triangular) lunate (cresent shaped) or bleached teeth.

In an embodiment of the invention, the generally rigid curing impression material includes a composition formulated from an isobutyl methacrylate based monomer combined in a volumetric mixture ratio relative to the isobutyl methacrylate based monomer of approximately 2 parts of the isobutyl methacrylate based monomer, 1 part of a dibutyl phthalate based plasticizer and 0.5 part of an amyl acetate based solvent.

In various embodiments of the invention, the cured impression material is essentially transparent when cured.

In another embodiment of the invention, a kit for making the anomalous appearing synthetic denture device is provided. The kit includes a first portion having one of a synthetic gum element having a plurality of individual and generally rigid novelty teeth bonded to at least a front surface of the synthetic gum element, or at least one generally rigid synthetic novelty tooth having an interior cavity.

The kit further includes a second portion having a plurality of compositions for preparing the generally rigid curing impression material including; a first container having a quantity of an alkyl-acrylic monomer stored therein; a second container having a quantity of an alkyl-phthalate ester plasticizer stored therein; an instruction booklet for preparing the first portion and the generally rigid curing impression material and a package for holding the first portion, the second portion, and the instruction booklet.

BRIEF DESCRIPTION OF DRAWINGS

The features and advantages of the invention will become apparent from the following detailed description when considered in conjunction with the accompanying drawings. Where possible, the same reference numerals and characters are used to denote like features, elements, components or portions of the invention. It is intended that changes and modifications can be made to the described embodiments without departing from the true scope and spirit of the subject invention as defined in the claims.

DETAILED DESCRIPTION

Figures 1, 1A:
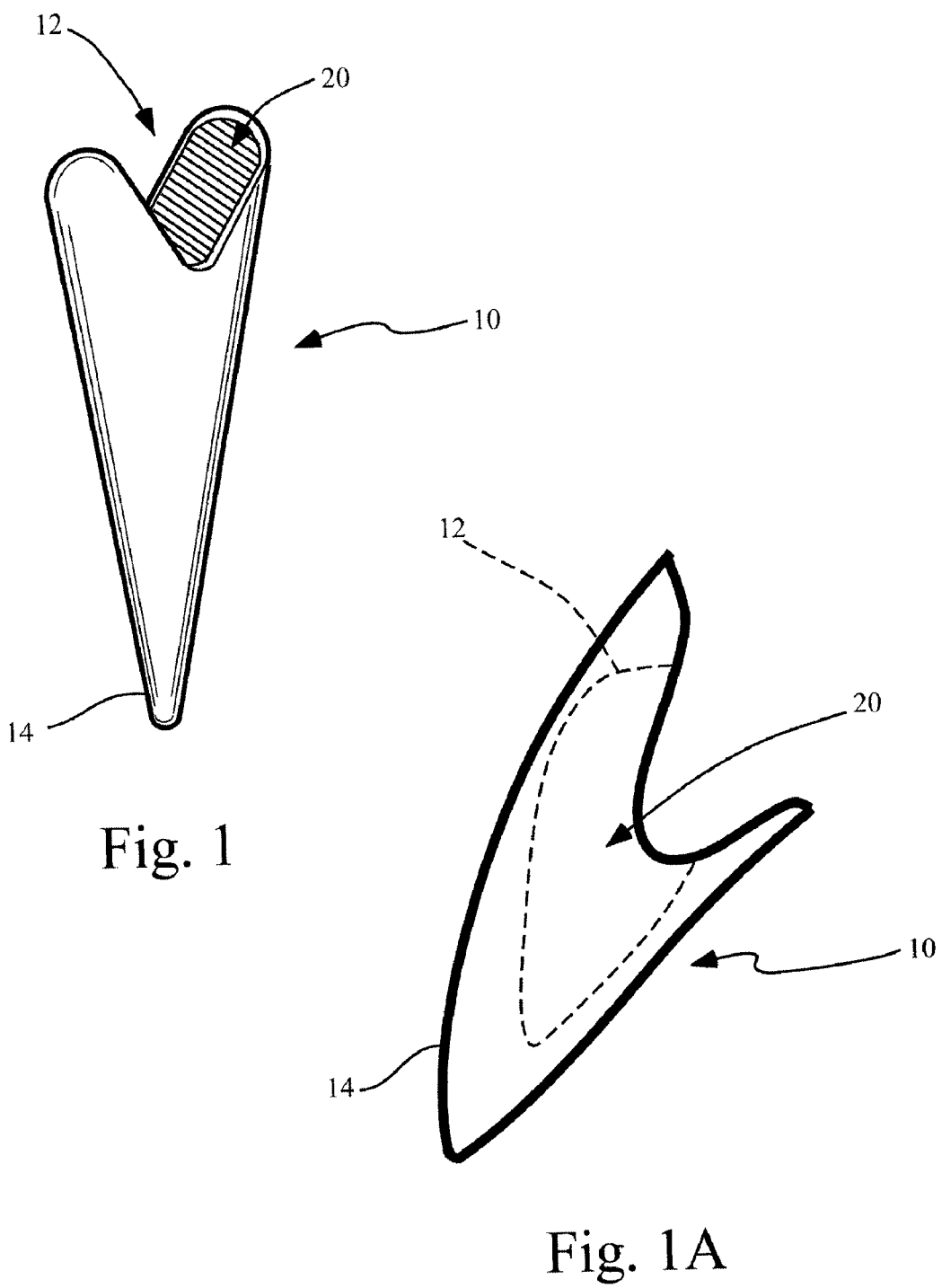
FIG. 1—is a prospective view of anomalous appearing synthetic tooth assembly.
FIG. 1A—is a side cross sectional veiw of an anomalous appearing synthetic tooth assembly FIG. 2—is a frontal view of the anomalous appearing synthetic tooth assembly.

Referring first to FIGS. 1 and 1A, an anomalous appearing synthetic denture device 10 is shown. In this embodiment of the invention, the novelty synthetic tooth 10 appears in the form of a molded plastic fang 14 and includes a generally rigid curing impression material 20. The materials used to make the synthetic tooth and impression materials are readily available from most chemical distributors and dental product supply companies.

For example, all of the chemical reagents and pigments described herein are available from Lang Dental Manufacturing Company, 175 Messner Drive, Wheeling, Ill. 60090; www.langdental.com. Pigments may be added to the synthetic tooth to create a realistic look. The plastic fang 14 is molded with an interior cavity 12 which roughly fits over a user's cuspid tooth. The interior cavity 12 of the synthetic 10 is intended to coaxially fit over a natural cuspid tooth.

Figure 2:
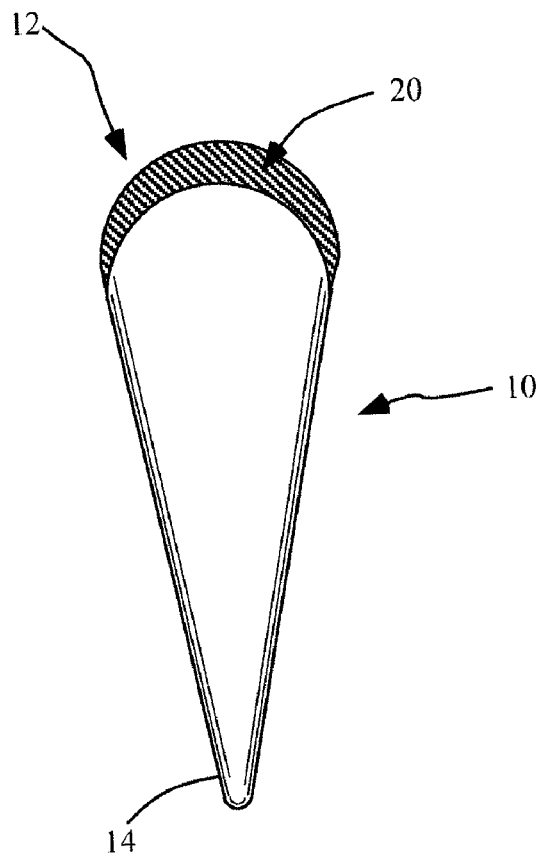
FIG. 2A—is a side cross sectional view of the anomalous appearing synthetic tooth assembly.
Figure 2A:
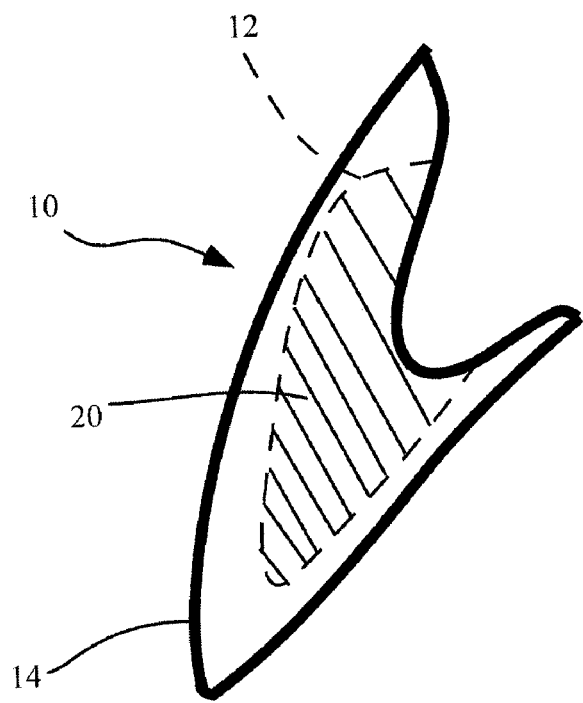
Figure 3:
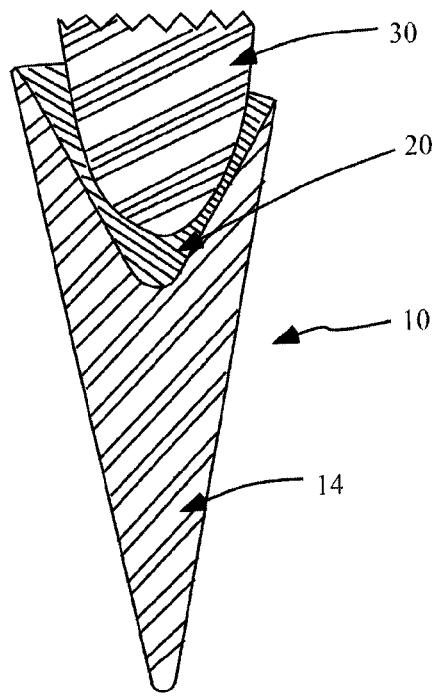
FIG. 3—is a first cross sectional view of the anomalous appearing synthetic denture device engaging a natural tooth.
Figure 3A:
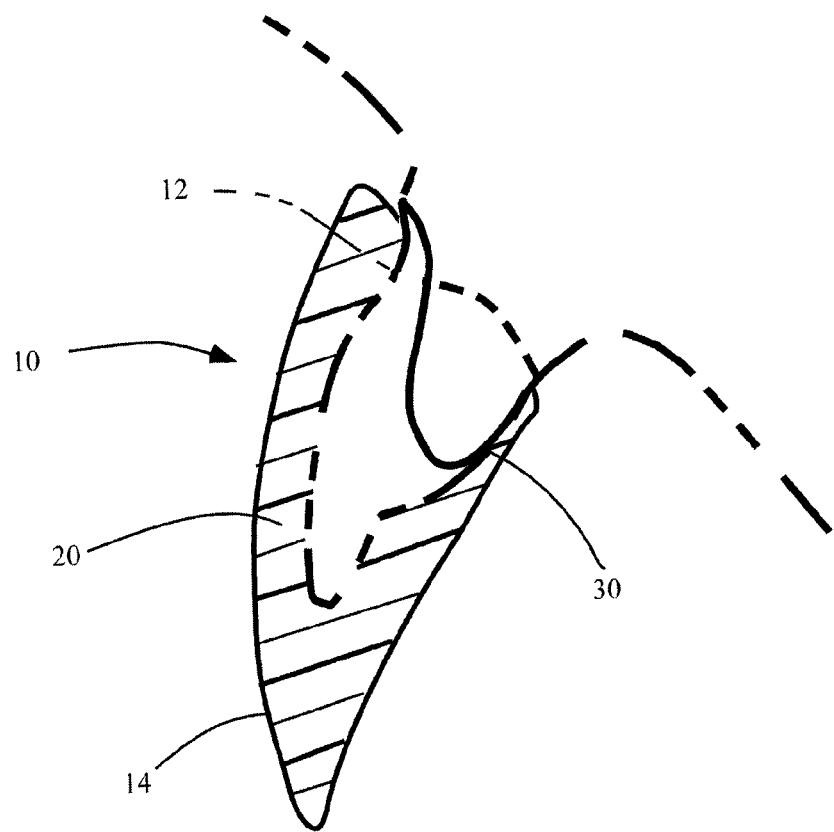
FIG. 3A—is a second cross sectional view of the anomalous appearing synthetic denture device engaging a natural tooth.

Referring to FIGS. 2 and 2A, the interior cavity 12 is filled with a pre-measured amount of the impression material 20 by a user. The impression material 20 is prepared by the user and placed within the interior cavity 12 of the synthetic tooth 10. The user then places the synthetic tooth 10 over the desired human tooth 30 (typically a cuspid) as is shown in FIGS. 3 and 3A.

Figure 3B:
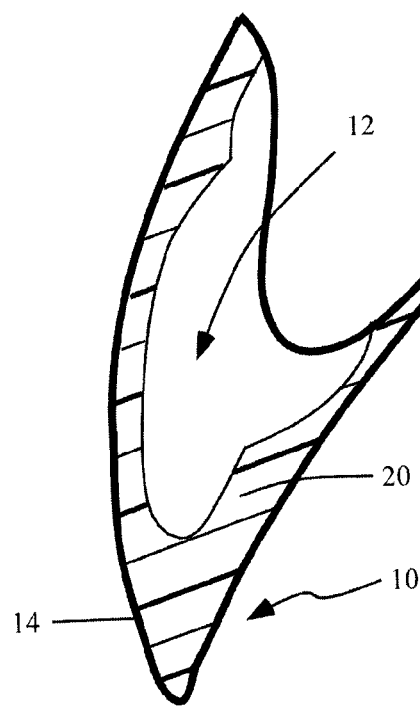
FIG. 3B—is a third cross sectional view of the anomalous appearing synthetic tooth illustrating the custom fit provided by the impression materiaL FIG. 3C—is a forth cross sectional view of the anomalous appearing synthetic tooth illustrating the tight fit provided by the impression material.
Figure 3C:
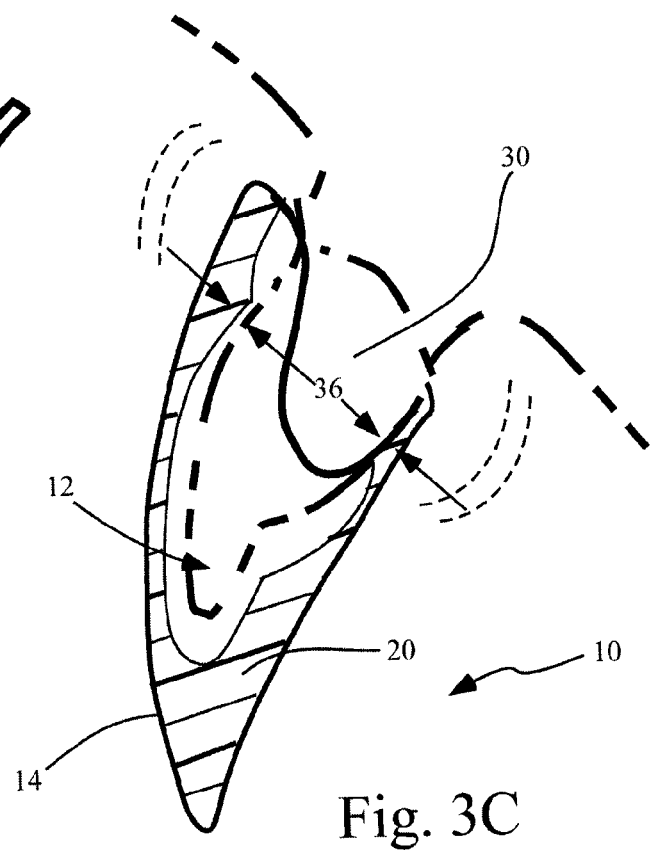

The impression material 20 is provided sufficient time to cure in place on the natural tooth 30. The generally rigid curing impression material 20 conforms to the outer surfaces of the natural tooth's enamel which provides a custom fit to the user's tooth as is shown in FIG. 3B. Natural contour or surface profile variations of the applied natural tooth 30, such as ridges, undercuts, depressions, pits, cracks, pores, etc., which allows the rigid setting impression material to form a tight (physio mechanical) fit 36 with the natural tooth 30. When fully cured, the impression material 20 allows the synthetic tooth 10 to be "snapped"36 into position over the natural tooth 30 as is shown in FIG 3C. The synthetic tooth 10 is secured in place by the tight fit 36 provided by the cured impression material 20 and surface adhesion at a saliva/impression material interface.

The constituents comprising the impression materials 20 are typically supplied in two part forms. When the two parts are combined, a generally rigid curing gel is formed. In general, the gel hardens or cures, in approximately five minutes depending on ambient temperature conditions but may require anywhere from three to ten minutes to fully cure.

In one embodiment of the invention, the user is provided with the molded plastic fang 14 or another style of anomalous appearing synthetic tooth and the impression material constituents.

The user first finds an accommodating location in his mouth for the synthetic novelty tooth 14. The user then combines the impression material components in accordance with the provided instructions to form the impression gel. The gel is applied to the interior cavity 12 of the synthetic novelty tooth 14. The synthetic novelty tooth assembly 10 (gel and synthetic novelty tooth) is then placed over one of the user's teeth 30 (generally a cuspid), or in some other selected location and held in the desired position for about five minutes.

After sufficient time has elapsed, the synthetic novelty tooth assembly 10 is then removed from the natural tooth. The impression material 20 is then generally affixed to the interior cavity 12 of the synthetic novelty tooth 14. One or more additional synthetic novelty teeth 14 may be prepared in an identical fashion.

The desirable properties of an ideal impression material includes the ability to form physio-mechanical interlocks with natural surface variations of one or more of the user's natural teeth including natural contour variations, interstitial spaces, undercuts, ridges, depressions, pits, cracks, pores, etc. The impression material should be sufficiently ductile to allow flexing for installation and removal and generally rigid in other circumstances to form the physio-mechanical interlocks with the natural teeth. Lastly, the ideal impression material should not be so rigid that the cured impression material becomes brittle and easily damaged. By experimentation, the inventor has created an ideal impression material suited for use with the novelty denture devices described herein.

An ideal acrylic resin impression material is provided by combining 2 parts by volume of an isobutyl methacrylate based monomer, with 1 part by volume of a dibutyl phthalate based plasticizer and 0.5 parts by volume of an amyl acetate based solvent.

Lang Dental Manufacturing Company provides the specific products containing these chemical constituents under their trade names of Isocryl Liquid 4006, Tempo Liquid 1066R and Bubblement Fragrance RRL-020. The specific chemical compositions of these constituents appear in there prospective material safety data sheets (MSDS) which are herein incorporated by reference in their entirety.

The synthetic novelty teeth may be manufactured in a variety of compositions including alkyl acrylic based plastics, polypropylene based plastics, acrylonitrile butadiene styrene (ABS) based plastics, polyethylene based plastics, polycarbonate based plastics, nylon based plastics, porcelain, stainless steel, titanium, silver or gold.

Likewise, the anomalous appearing synthetic novelty teeth may be manufactured in variety of different forms including non-homosapien teeth, metal encapsulated teeth, decayed teeth, deformed teeth, misaligned teeth, spicate (spike-shaped) teeth, sudiform (stake-like) teeth, stipiform (stalk-like) teeth, cuneate (triangular) lunate (cresent shaped) or bleached teeth.

Figure 4:
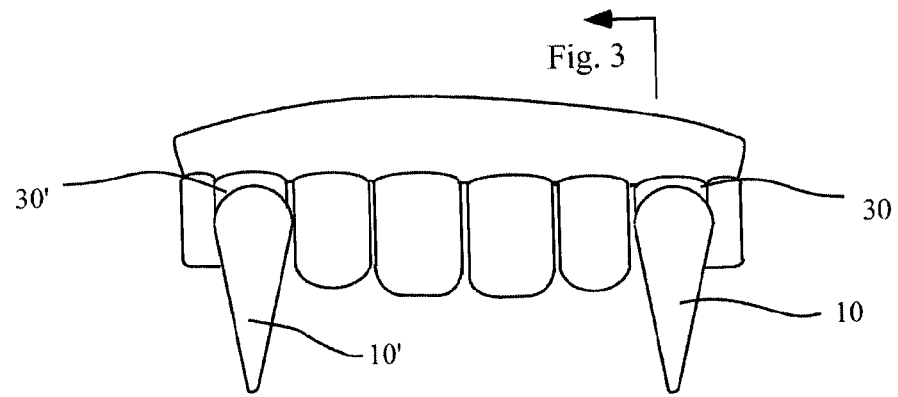
FIG. 4—is a frontal veiw of a pair of anomalous appearing synthetic tooth assemblies coupled to a user's upper cuspid teeth.

Referring to FIG. 4, a pair of synthetic novelty tooth assemblies 10, 10' is shown installed on the upper cuspids of a user. Although the displayed tooth form is that of fangs, such as would be needed for vampire role-playing, other novelty tooth forms are envisioned as well. The uses would include creating other desired themes for artificial teeth such as a werewolf, robot, mutant, movie character, ghoul, alien or other appearances.

Figure 5A:
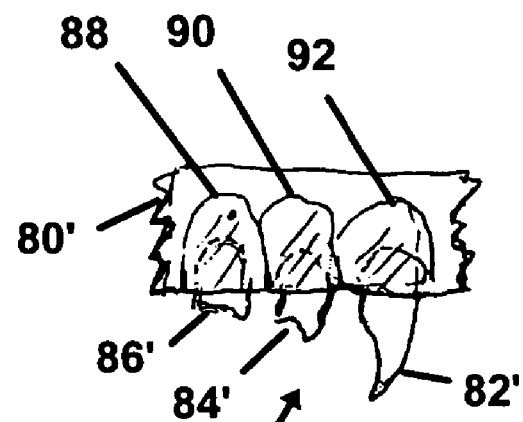
FIG. 5A—is a rear cutaway veiw of the synthetic denture assembly illustrating the custom fit provided by the impression material.
Figure 5:
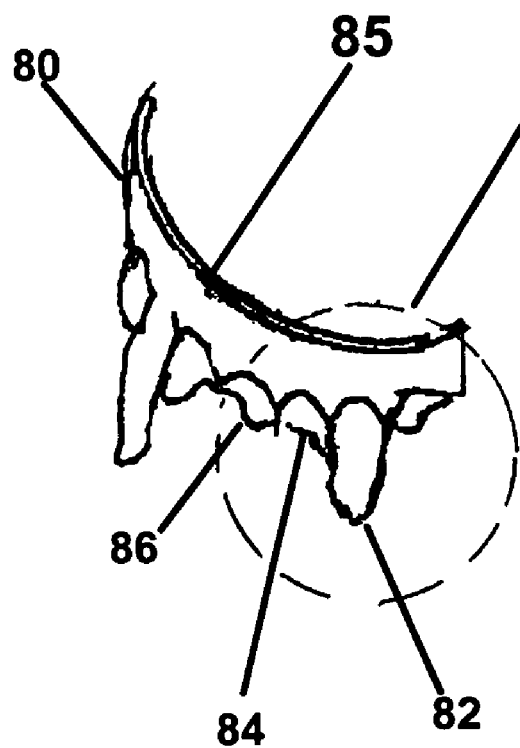
FIG. 5—is a perspective veiw of a synthetic denture assembly.

Referring to FIG. 5, an alternate embodiment of the invention is shown where the user is provided with an integral synthetic denture assembly 80. The integral synthetic denture assembly 80 is comprised of a series of individual synthetic novelty teeth 82, 84, 86 bonded to a relatively thin synthetic gum material 85.

The integral synthetic denture assembly 80 has a thickness in the range of 2-4 millimeters including the teeth and is configured in a generally arciform shape which conforms to the shape of the jaw. The height of the integral synthetic denture assembly 80 varies generally between 10-20 millimeters depending on the tooth forms bonded to the synthetic gum material 85. The overall length of the integral synthetic denture assembly 80 varies generally between 60-90 millimeters.

The synthetic novelty teeth 82, 84, 86 are bonded to the front surface of the synthetic gum primarily on the rear surfaces of the synthetic novelty teeth. Some additional bonding is provided at the top of the synthetic novelty teeth.

The synthetic denture assembly 80 is constructed by placing the individual synthetic novelty teeth in a mold with the proper orientation ("biting" edges down) and pouring a liquefied synthetic gum material over and around the synthetic novelty teeth. This technique is analogous to the technique described in U.S. Pat. No. 5,569,036 to the instant inventor and utilizes the same synthetic materials for the synthetic gum and teeth as described therein.

In this embodiment of the invention, a user combines the same impression material constituents, in the same proportions as described for the synthetic tooth to form the impression gel. The impression gel is then applied to the rear surface of the integral synthetic denture assembly 80. The integral synthetic denture assembly 80 is then placed in the mouth of the user and positioned against the front teeth and the impression material allowed to cure. As before, the gel cures, in approximately five minutes depending on ambient temperature conditions but may require anywhere from three to ten minutes to fully cured. Once the gel has cured, a generally rigid impression of the user's teeth 88, 90, 92 is formed on the rear surface of the synthetic denture assembly 80' as is shown in FIG. 5A.

The integral synthetic denture assembly 80 is secured in place by the tight fit provided by the cured impression material 80' and physio-mechanical interlocks previously described. This embodiment of the invention eliminates the mouth guard structure and bulkiness associated with the inventor's previous embodiment of the invention and provides a slim, custom fitting novelty denture which is more comfortable to wear. In both embodiments of the invention, the impression material cures to a generally rigid state and may or may not have tinting added. When no tinting is provided, the impression material cures to a generally transparent state.

Figure 6:
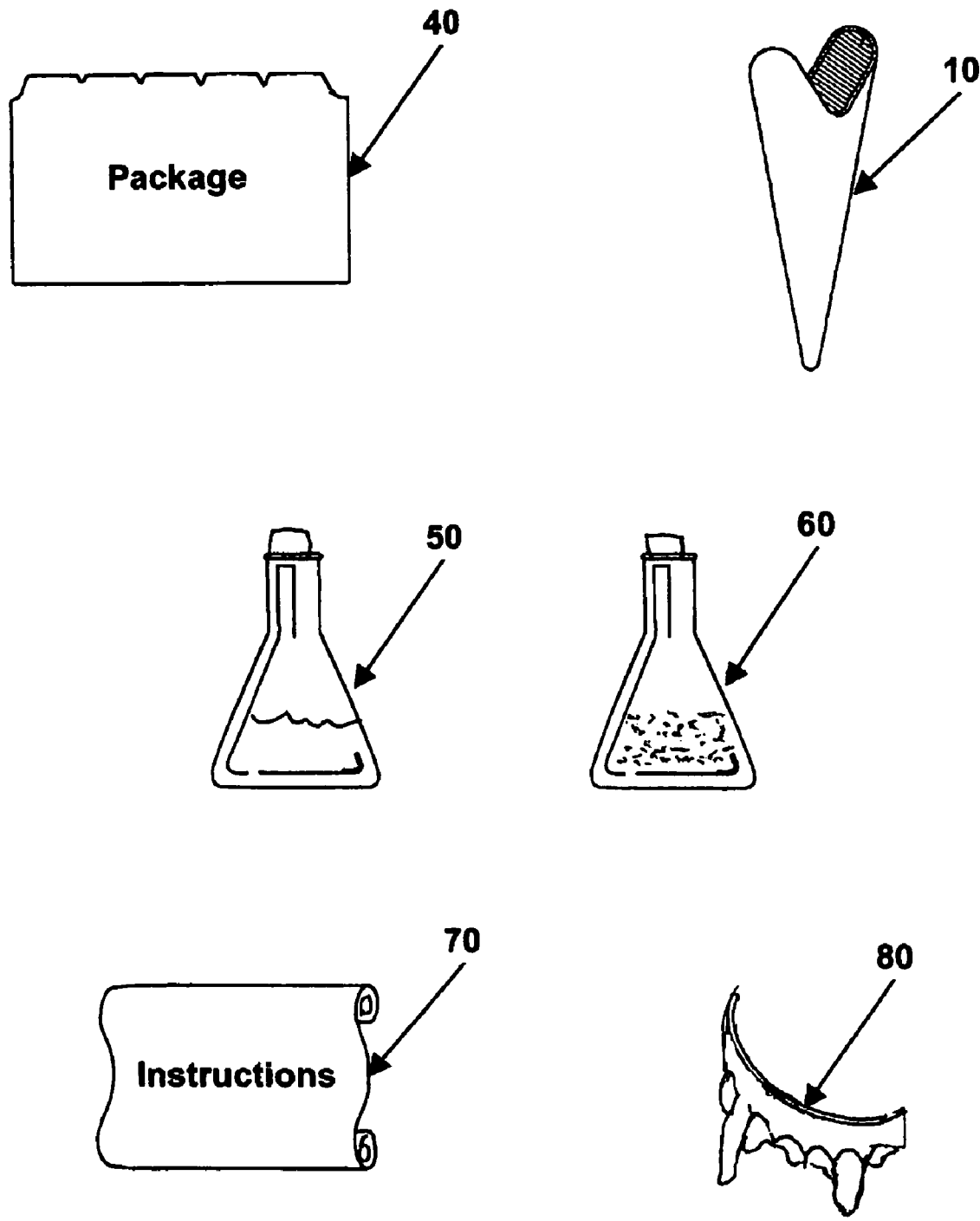
FIG. 6—is a kit form of the invention.

Referring to FIG. 6, a kit form of the invention is depicted. The kit is comprised of a first container 50 holding the isobutyl methacrylate based monomer, a second container 60 holding the dibutyl phthalate based plasticizer, either one or more novelty synthetic teeth 10 or the integral synthetic denture assembly 80, a set of instructions 70 and a package to hold the first container 50, second container 60, synthetic teeth 10 or integral synthetic denture assembly 80 and the set of instructions.

The foregoing described embodiments of the invention are provided as illustrations and descriptions. They are not intended to limit the invention to any one precise form described. In particular, it is contemplated that the invention described herein may be implemented using a different chemical species or slightly different chemical formulations of the reagents disclosed. No specific limitation is intended to a particular chemical supplier. Other variations and embodiments are possible in light of above teachings, and it is not intended that this Detailed Description limit the scope of invention, but rather by the claims following herein.

What is claimed:

1. A method of preparing an anomalous appearing synthetic denture device for use comprising:
   preparing a generally rigid curing impression material,
   placing at least a portion of said generally rigid curing impression material in contact with at least a portion of said anomalous appearing synthetic denture device,
   positioning said anomalous appearing synthetic denture device such that said generally rigid curing impression material encounters at least one human tooth,
   allowing a sufficient amount of time for said generally rigid curing impression material to cure, and
   removing said anomalous appearing synthetic denture device from said at least one human tooth;
   wherein said generally rigid curing impression material comprises a volumetric mixture ratio relative to an isobutyl methacrylate based monomer of approximately 2 parts of said isobutyl methacrylate based monomer, 1 part of a dibutyl phthalate based plasticizer and 0.5 part of an amyl acetate based solvent.

2. The method according to claim 1 wherein said anomalous appearing synthetic denture device comprises at least one generally rigid synthetic novelty tooth having an interior cavity.

3. The method according to claim 2 wherein said placing further includes disposing at least a portion of said generally rigid curing impression material into said interior cavity forming a synthetic novelty tooth assembly.

4. The method according to claim 3 wherein said positioning further includes coaxially positioning said synthetic novelty tooth assembly over said at least one human tooth such that said interior cavity encapsulates at least a portion of said at least one human tooth.

5. The method according to claim 2 wherein said at least one generally rigid synthetic novelty tooth comprises a composition selected from the group consisting of an alkyl acrylic based plastic, an acrylonitrile butadiene styrene based plastic, a polyethylene based plastic, polypropylene based plastic, a polycarbonate based plastic, a nylon based plastic, porcelain, stainless steel, titanium, silver and gold.

6. The method according to claim 1 further including reaffixing said anomalous appearing synthetic denture device when desired for use.

7. The method according to claim 1 wherein said anomalous appearing synthetic denture device comprises a plurality of synthetic novelty teeth which are individually bound to at least a front side of a somewhat flexible synthetic gum element forming an integral synthetic denture assembly.

8. The method according to claim 7 wherein said placing further includes spreading said at least a portion of generally rigid curing impression material on a rear surface of said integral synthetic denture assembly.

9. The method according to claim 7 wherein said positioning further includes arranging said rear surface of said integral synthetic denture assembly such that said generally rigid curing impression material encounters said at least one human tooth.

10. The method according to claim 1 wherein said generally rigid curing impression material forms a tight fit when cured with a plurality of natural contour variations associated with said at least one human tooth.

11. The method according to claim 1 wherein said sufficient time is less than 10 minutes.

12. The method according to claim 1 wherein said sufficient time is in a range of 3 to 10 minutes.

13. The method according to claim 1 wherein said generally rigid curing impression material comprises at least one alkyl-acrylic monomer selected from the group consisting of isobutyl methacrylate, methyl methylacrylate, ethyl methacrylate, N-butyl methacrylate, trimethyipropane trimethacrylate and polymethyl methacrylate.

14. The method according to claim 13 wherein said generally rigid curing impression material further comprises at least one alkyl-phthalate ester plasticizer selected from the group consisting of dialkyl phthalate, dibutyl phthalate and N,N-dimethyl-p-toluidine.

15. The method according to claim 14 wherein said generally rigid curing impression material further comprises at least one organic solvent selected from the group consisting of denatured ethanol, amyl acetate, ethyl acetate and isobutyl acetate.

16. The method according to claim 1 wherein said generally rigid curing impression material has at least one physical property selected from the group consisting of essentially transparent when cured, forms physio-mechanical interlocks with said at least one human tooth, sufficiently ductile to allow flexing for installation and removal and generally non-brittle.

17. A method of preparing an anomalous appearing novelty tooth assembly, comprising:
providing a novelty tooth,
wherein said novelty tooth is shaped to resemble a fang, and
wherein the fang comprises at least one tooth form selected from a group consisting essentially of a non-homo-sapien tooth form, a metal-encapsulated tooth form, a decayed tooth form, a deformed tooth form, a misaligned tooth form, a spicate tooth form, a sudiform tooth form, a stipiform tooth form, a cuneate tooth form, a lunate tooth form, and a bleached tooth form;
preparing a rigid curing impression material;
disposing at least a portion of said prepared impression material within an interior cavity of said novelty tooth;
coaxially positioning said novelty tooth over a human tooth such that said impression material disposed within said cavity contacts a plurality of natural surface variations associated with said human tooth;
allowing a predetermined amount of time for said impression material to harden into a ductile impression of said human tooth, said hardened ductile impression including a plurality of physio-mechanical interlocks which conform with said plurality of natural surface variations, and said hardened ductile impression and said novelty tooth forming a novelty tooth assembly; and
removing said novelty tooth assembly from said human tooth after said predetermined amount of time has elapsed,
thereby providing conformability of said plurality of physio-mechanical interlocks with said plurality of natural surface variations via snapping said novelty tooth assembly into position over said human tooth in operation,
thereby providing a tight fit between said novelty tooth assembly and said human tooth by way of the rigid curing impression material, and
thereby providing the novelty tooth assembly as being temporarily disposable over at least one natural human tooth during use, wherein the at least one natural human tooth comprises at least one element selected from a group consisting essentially of an uncut natural human tooth, an undamaged natural human tooth, and a whole natural human tooth.

18. The method according to claim 17 wherein said physio-mechanical interlocks provides a tight fit on said human tooth when said novelty tooth assembly is coupled thereto.

19. The method according to claim 17 wherein said impression material is sufficiently ductile when hardened for removing and reaffixing said novelty tooth assembly with said human tooth without damaging said hardened impression.

20. The method according to claim 19 wherein said reaffixing comprises:
positioning said novelty tooth assembly such that said cavity is aligned to receive said human tooth; and
placing said novelty tooth assembly over said human tooth such that said plurality of physio-mechanical interlocks of said hardened impression conform with said plurality of natural surface variations.

21. The method according to claim 20 wherein said anomalous appearing novelty tooth assembly remains tight-fitted to said human tooth without usage of denture adhesives.

22. The method, according to claim 17,
wherein said physio-mechanical interlocks provides a tight fit on said human tooth when said novelty tooth assembly is coupled thereto,
wherein said impression material is sufficiently ductile when hardened for removing and reaffixing said novelty tooth assembly with said human tooth without damaging said hardened impression,
wherein said reaffixing comprises:
positioning said novelty tooth assembly such that said cavity is aligned to receive said human tooth; and
placing said novelty tooth assembly over said human tooth such that said plurality of physio-mechanical interlocks of said hardened impression conform with said plurality of natural surface variations, and
wherein said anomalous appearing novelty tooth assembly remains tight-fitted to said human tooth without usage of denture adhesives.

23. An anomalous appearing novelty tooth assembly, comprising:
a novelty tooth,
wherein said novelty tooth is shaped to resemble a fang, and
wherein the fang comprises at least one tooth form selected from a group consisting essentially of a non-homo-sapien tooth form, a metal-encapsulated tooth form, a decayed tooth form, a deformed tooth form, a misaligned tooth form, a spicate tooth form, a sudiform tooth form, a stipiform tooth form, a cuneate tooth form, a lunate tooth form, and a bleached tooth form;
a cavity disposed in one end of said novelty tooth,
said cavity including a hardened, but ductile, impression of a human tooth coaxially contained therein,
said hardened impression formed from a rigid curing impression material allowed to harden for a predetermined amount of time while in contact with said human tooth,
said impression material forming a plurality of physio-mechanical interlocks which conform to a plurality of natural surface features of said human tooth when hardened,
wherein said hardened impression and said novelty tooth form a novelty tooth assembly,
wherein said plurality of physio-mechanical interlocks conform with said plurality of natural surface variations via snapping said novelty tooth into position over said human tooth in operation,
wherein a tight fit is provided between said novelty tooth and said human tooth by way of the rigid curing impression material,
wherein the novelty tooth assembly is temporarily disposable over at least one natural human tooth during use,
wherein the at least one natural human tooth comprises at least one element selected from a group consisting essentially of an uncut natural human tooth, an undamaged natural human tooth, and a whole natural human tooth, and
wherein said impression material is sufficiently ductile when hardened to allow for removal and reaffixing of said novelty tooth assembly with said human tooth without damaging said hardened impression.

24. The anomalous appearing novelty tooth assembly, according to claim 23, wherein said plurality of physio-mechanical interlocks provides a tight fit on said human tooth when said novelty tooth assembly is coupled thereto.

25. The anomalous appearing novelty tooth assembly, according to claim 23, wherein said reaffixing comprises:
positioning said novelty tooth assembly such that said cavity is aligned to receive said human tooth; and placing said novelty tooth assembly over said human tooth such that said plurality of physio-mechanical interlocks of said hardened impression conform with said plurality of natural surface features.

26. The anomalous appearing novelty tooth assembly, according to claim 25 wherein said anomalous appearing novelty tooth assembly remains tight-fitted to said human tooth without usage of denture adhesives.

27. An anomalous appearing novelty tooth assembly, according to claim 23, wherein the rigid curing impression material comprises a monomer and a plasticizer.

28. An anomalous appearing novelty tooth assembly, according to claim 27, wherein the plasticizer comprises at least one alkyl-pthalate ester plasticizer selected from a group consisting essentially of dialkyl phtalate and dibutyl phtalate.

29. An anomalous appearing novelty tooth assembly, according to claim 23,
- wherein said plurality of physio-mechanical interlocks provides a tight fit on said human tooth when said novelty tooth assembly is coupled thereto,
- wherein said impression material is sufficiently ductile when hardened to allow for removal and reaffixing of said novelty tooth assembly with said human tooth without damaging said hardened impression,
- wherein said reaffixing comprises: positioning said novelty tooth assembly such that said cavity is aligned to receive said human tooth; and placing said novelty tooth assembly over said human tooth such that said plurality of physio-mechanical interlocks of said hardened impression conform with said plurality of natural surface features,
- wherein said anomalous appearing novelty tooth assembly remains tight-fitted to said human tooth without usage of denture adhesives,
- wherein the rigid curing impression material comprises a monomer and a plasticizer, and
- wherein the plasticizer comprises at least one alkyl-pthalate ester plasticizer selected from a group consisting essentially of dialkyl phtalate and dibutyl phthalate.

* * * * *